US 7,850,601 B2

(12) United States Patent
Uchimura et al.

(10) Patent No.: US 7,850,601 B2
(45) Date of Patent: Dec. 14, 2010

(54) ENDOSCOPE HAVING NON-CONTACT CHARGING APPARATUS

(75) Inventors: Sumihiro Uchimura, Samihara (JP); Akira Taniguchi, Hachioji (JP); Fumiyuki Onoda, Tama (JP); Toshiaki Noguchi, Tachikawa (JP); Katsuya Suzuki, Sagamihara (JP)

(73) Assignee: Olympus Corporation, Tokyo (JP)

( * ) Notice: Subject to any disclaimer, the term of this patent is extended or adjusted under 35 U.S.C. 154(b) by 1100 days.

(21) Appl. No.: 11/545,271

(22) Filed: Oct. 10, 2006

(65) Prior Publication Data

US 2007/0032698 A1 Feb. 8, 2007

Related U.S. Application Data

(63) Continuation of application No. PCT/JP2005/006873, filed on Apr. 7, 2005.

(30) Foreign Application Priority Data

Apr. 8, 2004 (JP) .............................. 2004-114718

(51) Int. Cl.
*A61B 1/04* (2006.01)
(52) U.S. Cl. .................... 600/118; 600/103; 600/109
(58) Field of Classification Search .................. 600/103, 600/109, 130, 117, 118, 146
See application file for complete search history.

(56) References Cited

U.S. PATENT DOCUMENTS 4,879,991 A * 11/1989 Ogiu ........................... 600/129

| 6,099,465 | A | * | 8/2000 | Inoue | 600/134 |
| 6,494,827 | B1 | * | 12/2002 | Matsumoto et al. | 600/118 |
| 2003/0069475 | A1 | | 4/2003 | Banik et al. | |
| 2005/0187434 | A1 | * | 8/2005 | Dey et al. | 600/179 |
| 2006/0022234 | A1 | * | 2/2006 | Adair et al. | 257/292 |
| 2006/0293562 | A1 | * | 12/2006 | Uchimura et al. | 600/110 |
| 2008/0167528 | A1 | * | 7/2008 | Segawa et al. | 600/160 |
| 2009/0036739 | A1 | * | 2/2009 | Hadani | 600/121 |

FOREIGN PATENT DOCUMENTS

| JP | 06-054794 | | 3/1994 |
| JP | 10-258028 | | 9/1998 |
| JP | 10-295635 | | 11/1998 |
| JP | 11-056774 | | 3/1999 |
| JP | 2001-083433 | | 3/2001 |
| JP | 2002165388 A | * | 6/2002 |
| JP | 2002177217 A | * | 6/2002 |
| JP | 2003-088499 | | 3/2003 |
| JP | 2004-065832 | | 3/2004 |

* cited by examiner

*Primary Examiner*—John P Leubecker
(74) *Attorney, Agent, or Firm*—Scully, Scott, Murphy & Presser, P.C.

(57) ABSTRACT

The endoscope has an elongated insertion portion, an operation portion provided at the rear end of the insertion portion, and a contact-less endoscope exterior body in which no electrical contact is exposed on the outer surface thereof including the insertion portion and the operation portion. Inside the endoscope exterior body, there are disposed an image pickup apparatus for picking up images and a signal processing portion for performing signal processing for the image pickup apparatus. The endoscope comprises a battery of a water-tight structure for supplying power for the image pickup apparatus and the signal processing portion, and a charging apparatus of a water-tight structure for charging the battery with power supplied in a contact-less fashion.

19 Claims, 13 Drawing Sheets

ENDOSCOPE HAVING NON-CONTACT CHARGING APPARATUS

CROSS REFERENCE TO RELATED APPLICATION

This application is a continuation application of PCT/JP 2005/006873 filed on Apr. 7, 2005 and claims benefit of Japanese Application No. 2004-114718 filed in Japan on Apr. 8, 2004, the entire contents of which are incorporated herein by this reference.

BACKGROUND OF THE INVENTION

1. Field of the Invention

The present invention relates to an endoscope for performing endoscope inspection etc. by being inserted into a body cavity or the interior of various equipment.

2. Description of the Prior Art

Recently, endoscopes have been widely adopted for optical inspection and diagnosis in medical and industrial fields.

In order to realize portability, there has been proposed an endoscope in which a battery is provided in the endoscope body. For example, Japanese Patent Laid-Open No. 2001-83433 discloses an endoscope in which a light source unit incorporating a rechargeable battery is detachably provided in the operation portion of the endoscope body. In the prior art example according to the above publication, there is provided a battery for generating electric power to operate illumination means.

Further, Japanese Patent Laid-Open No. 10-295635 discloses an electronic endoscope having a near contact-less structure and exemplarily incorporating a battery. Moreover, the Japanese Patent Laid-Open No. 10-295635 describes a structure exemplarily incorporating a battery.

SUMMARY OF THE INVENTION

The endoscope of the present invention includes an elongated insertion portion and an operation portion provided at the rear end of the insertion portion; incorporates an image pickup apparatus and a signal processing portion for performing signal processing for the image pickup apparatus; and has a contact-less structure, the endoscope comprising a battery of a watertight structure for supplying electric power to at least the image pickup apparatus and the signal processing portion, and a charging portion of a watertight structure for charging the battery through the power supplied in a contact-less fashion.

DETAILED DESCRIPTION OF THE PREFERRED EMBODIMENTS

Figure 1:
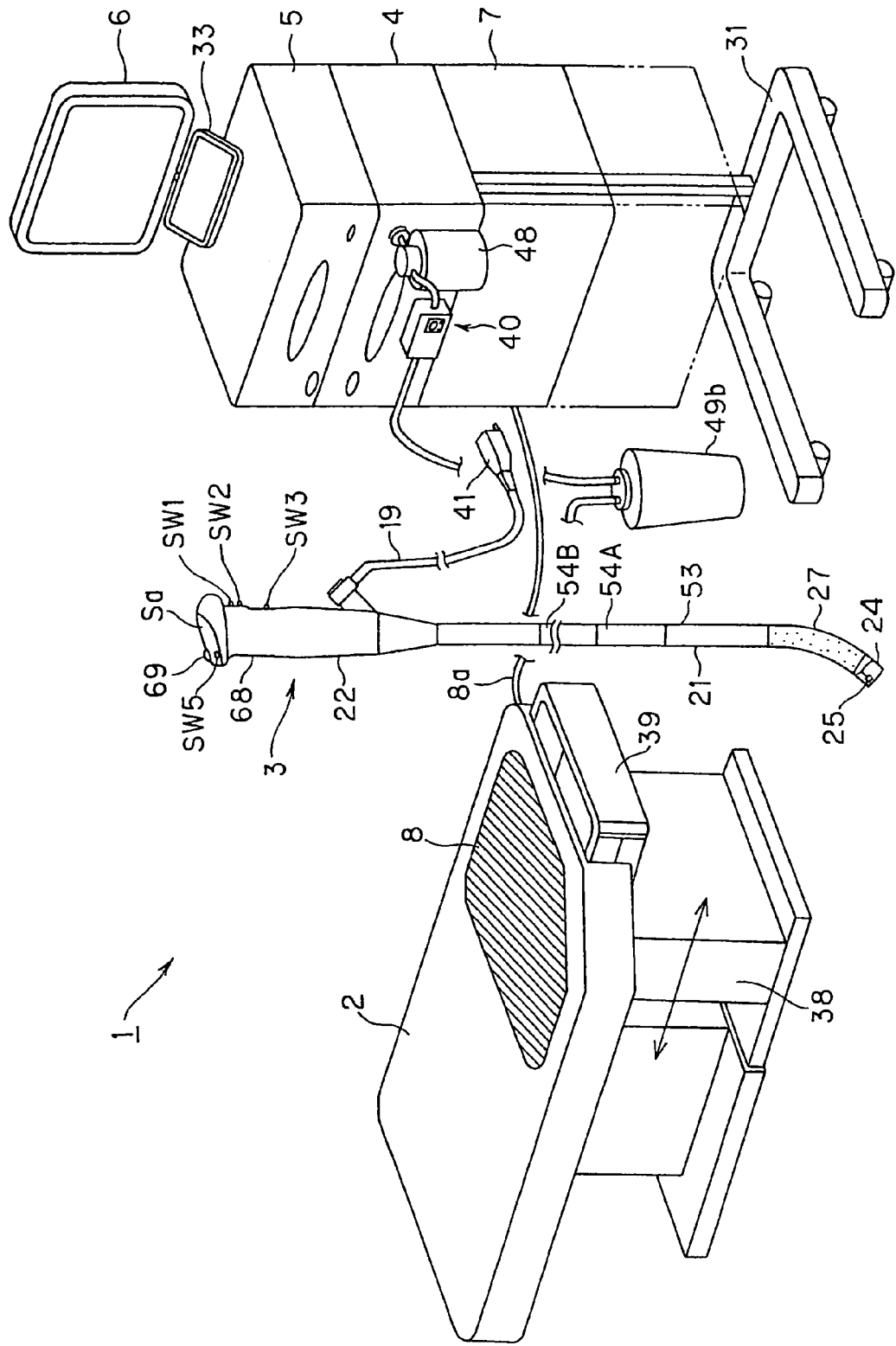
FIG. 1 is a configuration diagram to show the schematic configuration of an endoscope system.

As shown in FIG. 1, an endoscope system 1 including the first embodiment of the present invention comprises a flexible endoscope (also referred to as a scope) 3 which is used in endoscope inspection by being inserted into a body cavity of a patient (not shown) lying on an inspection bed 2; an air feed/water feed/suction unit (hereinafter abbreviated as an AWS unit) 4 having air supply, water supply, and suction functions and to which the endoscope 3 is connected; an endoscope system control apparatus 5 for performing signal processing for an image pickup element incorporated in the endoscope 3, control processing for various operation means provided in the endoscope 3, and video processing etc.; an observation monitor 6 based on a liquid crystal monitor etc. for displaying a video signal generated by the endoscope system control apparatus 5. Moreover, the observation monitor 6 is provided with a touch panel 33.

Further, the endoscope system 1 comprises a image recording unit 7 for filing, for example, digital video signals generated by the endoscope system control apparatus 5; and a UPD coil unit 8 which is connected to the AWS unit 4 and when a shape detection coil (hereinafter abbreviated as a UPD coil) is incorporated in the insertion portion of the endoscope 3, detects the position of each UPD coil by receiving electromagnetic field through the UPD coil to display the shape of the insertion portion of the endoscope 3.

In the case shown in FIG. 1, the UPD coil unit 8 is provided so as to be embedded in the upper face of the inspection bed 2. This UPD coil unit 8 is connected with the AWS unit 4 through a cable 8a.

Further, in the present embodiment, there is provided a housing recess at one end of the inspection bed 2 in the longitudinal direction and at a location underneath thereof so that a tray-carrying trolley 38 can be housed therein. On the top of this tray-carrying trolley 38, there is placed a scope tray 39 in which the endoscope 3 having a water tight structure is contained.

Thus, the scope tray 39 containing the endoscope 3 which has been sterilized or disinfected can be carried by the tray-carrying trolley 38 and to be housed in the housing recess of the inspection bed 2. The operator may pull out the endoscope 3 from the scope tray 39 to use it for endoscope inspection, and house it in the scope tray 39 again after completing endoscope inspection. Thereafter, sterilization or disinfection can be performed smoothly by carrying the scope tray 39 containing the endoscope 3 after use with the tray-carrying trolley 38.

Further, in this embodiment, the AWS unit 4 and the endoscope system control apparatus 5 shown in FIG. 1 are configured to transmit and receive information (data) with each other based on wireless scheme. Although the endoscope 3 is connected with the AWS unit 4 by a tube unit 19 in FIG. 1, the transmit and receive (two-way transmission) of information (data) will be performed based on wireless scheme as described later. Moreover, the endoscope system control apparatus 5 also transmits and receives information to and from the endoscope 3 and the AWS unit 4 based on wireless scheme.

Further, as shown in FIG. 1, the endoscope 3 of the embodiment 1 comprises an endoscope body 18 and the tube unit 19 which is detachably connected to the endoscope body 18 and is, for example, of a throwaway type (a disposable pipe). The above described endoscope body 18 comprises an elongated flexible insertion portion 21 to be inserted into a body cavity, and an operation portion 22 provided at the rear end of the insertion portion 21, the operation portion 22 being detachably connected with the base end of the tube unit 19.

At the tip end portion 24 of the above described insertion portion 21, there is provided an image pickup unit which utilizes as the image pickup element a charge coupled device (abbreviated as CCD) 25 which provides a variable gain within the image pickup element. At the rear end of the above described tip end portion 24, there is provided a bending portion 27 which can be bent with a small amount of force, and the bending portion 27 can be bent by operating a trackball 69 as the operation means (instruction-input portion) provided in the operation portion 22. This trackball 69 can be used for angle operation (bending operation) as well as for changing the settings of other functions of the scope switch, for example, the settings of angle sensitivity, air feed amount, etc.

Further, the above described insertion portion 21 is formed at multiple locations with rigidity varying portions which are provided with rigidity varying actuators 54A and 54B for allowing the rigidity variable so that inserting operation etc. may be more smoothly performed.

Figure 3:
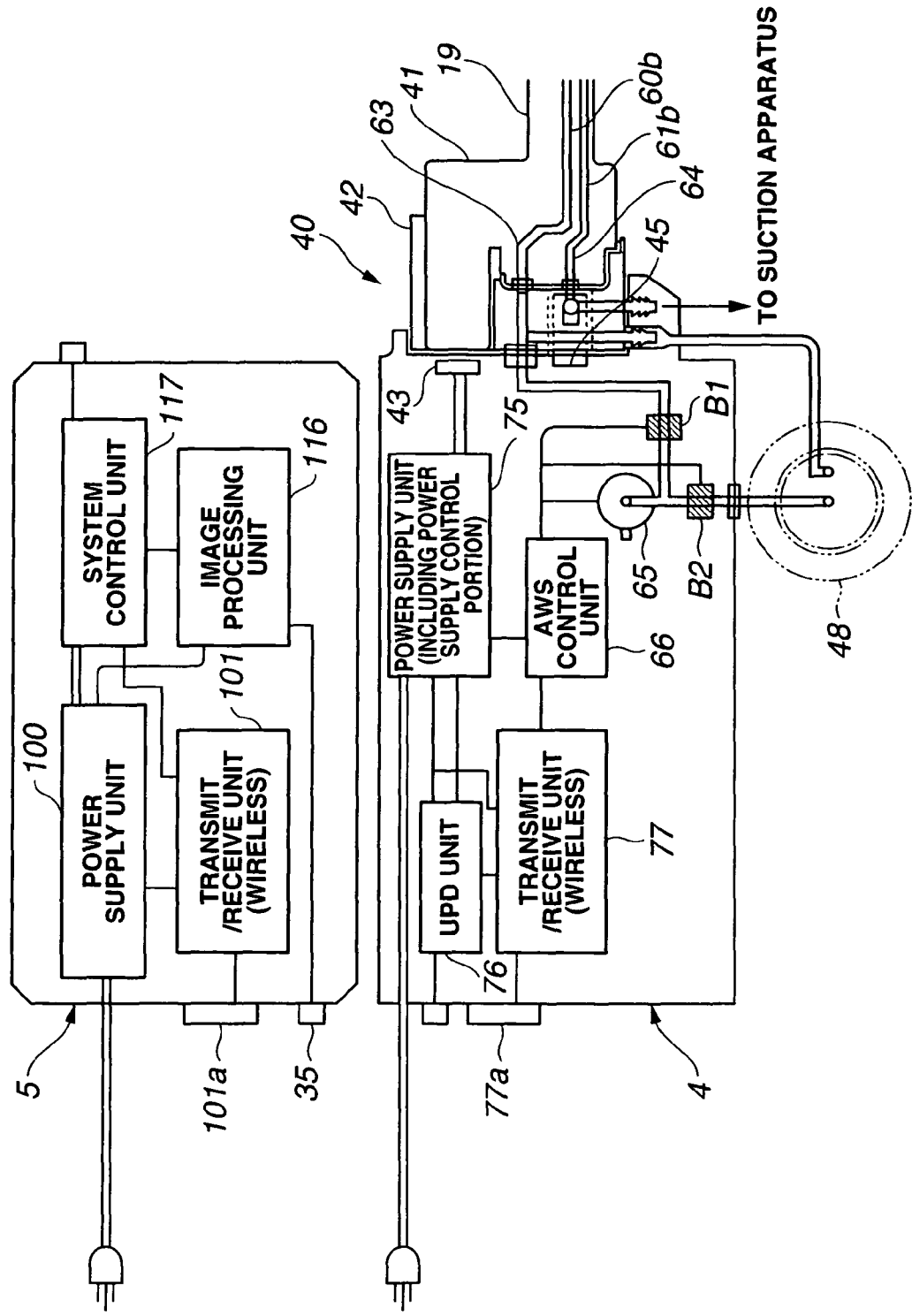
FIG. 3 shows the internal configuration of an endoscope system control apparatus and an AWS unit, and the structure of the connection portion of a scope connector.

In this embodiment, the AWS unit 4 and the endoscope system control apparatus 5 transmit and receive data with each other through, for example, a wireless transmit/receive unit 77, 101 as shown in FIG. 3. Moreover, the observation monitor 6 is connected to a monitor connector 35 of the endoscope system control apparatus 5 through a monitor cable.

The endoscope system control apparatus 5 comprises a power supply unit 100, the transmit/receive unit 101 which is supplied with power from the power supply unit 100, an image processing unit 116 for performing image processing, and a system control unit 117 for controlling the entire system, the transmit/receive unit 101 being connected to an antenna portion 101a.

The AWS unit 4 comprises a power supply unit 75, the transmit/receive unit 77 which is supplied with power from the power supply unit 75, a UPD unit 76 for generating image data for the position of the insertion portion of the endoscope 3 (a UPD image) detected using the UPD coil unit 8, and an AWS control unit 66 for performing AWS control, the transmit/receive unit 77 being connected to an antenna portion 77a.

Then, to the endoscope system control apparatus 5, image data picked up by a CCD 25 are transmitted from the endoscope 3, and also image data of the UPD image are transmitted from the AWS unit 4. Thus, the endoscope system control apparatus 5 transmits video signals corresponding to these image data to the observation monitor 6 so that the UPD image as well as the endoscope image can be displayed on the display screen thereof.

The observation monitor 6 is constructed of a high definition TV (HDTV) monitor so that multiple kinds of images can be displayed simultaneously on its display screen.

Further, as shown in FIG. 1, the AWS unit 4 is provided with, for example, a scope connector 40. To this scope connector 40, a scope connector 41 of the endoscope 3 is detachably connected.

In this case, the scope connector 40 on the AWS unit 4 comprises an AWS adaptor 42 having a structure to allow the connection with the connector 41 at the end of the tube unit 19, in which only a conduit is provided as in the endoscope 3 of the embodiment 1, and also with a connector (not shown) for the case in which a signal line is inserted into the tube unit 19 (see FIG. 3).

Figure 2:
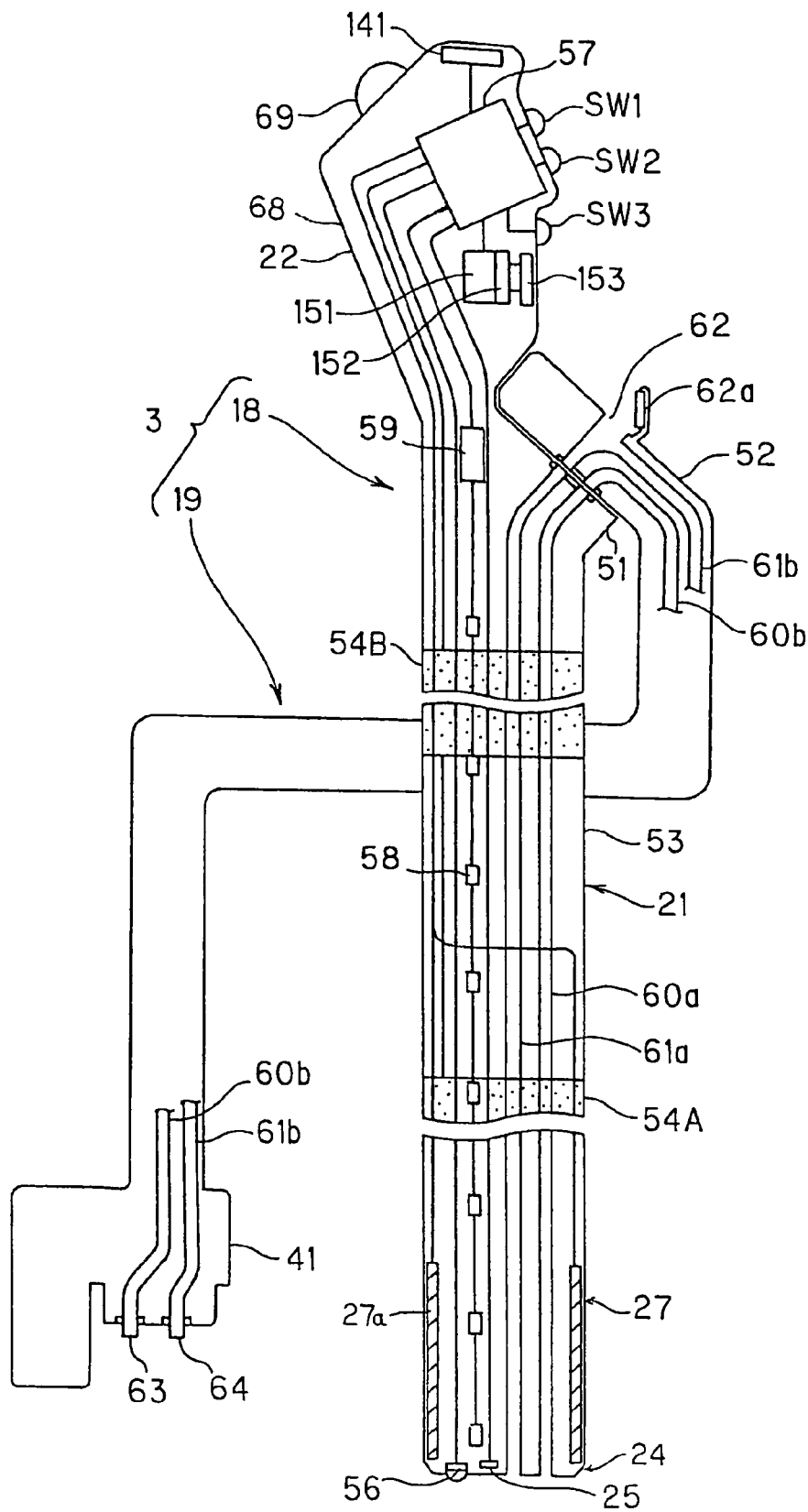
FIG. 2 is a general view to show detailed configuration of the endoscope.

Referring to FIG. 2, next, specific configuration of the endoscope 3 according to the first embodiment 1 of the present invention will be described.

As generally described in FIG. 1, a flexible endoscope 3 comprises the endoscope body 18 having an elongated, flexible insertion portion 21 and an operation portion 22 provided at the rear end thereof; and the tube unit 19 of a throwaway type (a disposable type), wherein the connector portion 52 provided at the base end of the tube unit 19 is detachably connected to the connector portion 51 for connecting the tube unit, provided in the vicinity of the base end (front end) of the operation portion 22 in the endoscope body 18.

At the end of the tube unit 19, there is provided the above described scope connector 41 which is detachably connected to the AWS unit 4.

The insertion portion 21 comprises the hard tip end portion 24 provided at the tip end of the insertion portion 21, a bendable bending portion 27 provided at the rear end of the tip end portion 24, and an elongated, flexible portion (hose portion) 53 extending from the rear end of the bending portion 27 to the operation portion 22. At multiple locations in the middle of the flexible portion 53, specifically at two locations, there are provided rigidity varying actuators 54A and 54B formed of an electroconductive polymer artificial muscle (abbreviated as EPAM) which can be expanded and contracted, and also changed in hardness by applying a voltage.

Inside an illumination widow provided at the tip portion 24 of the insertion portion 21, there is attached, for example, a light emitting diode (abbreviated as LED) 56 as the illumination means, and the illumination light of the LED 56 is projected forwardly through an illumination lens integrally attached to the LED 56 to illuminate an object to be observed such as an affected part. The light emitting element for forming the illumination means will not be limited by the LED 56, and may be formed using a LD (laser diode), and the like.

Further, the observation window provided adjacent to the illumination widow is attached with an object lens (not shown), at which image forming position, the CCD 25 incorporating a variable gain function is disposed thereby forming image pickup means for picking up the image of an object. A signal line which inserted into the insertion portion 21 with its one end being connected to the above described LED 56 and CCD 25 respectively, is connected to a control circuit 57 which is provided inside the operation portion 22 and performs intensive control processing (collective control processing).

In the above described insertion portion 21, there are disposed a plurality of UPD coils 58 at a predetermined space in the longitudinal direction, and the signal line connected to each UPD coil 58 is connected to the control circuit 57 via a UPD coil driving unit 59 provided in the operation portion 22.

Further, at four locations in the circumferential direction of the inner wall of the casing of the bending portion 27, there is disposed an angular actuators 27a as the angle element (bend element) formed by disposing EPAMs in its longitudinal direction. This angular actuator 27a and the rigidity varying actuator 54A and 54B are also connected to the control circuit 57 respectively via a signal line. The control circuit 57 is constructed by, for example, implementing electronic circuit elements on a switch board 57a and a trackball board 57b.

The EPAM used for the angular actuator 27a and the rigidity varying actuators 54A, 54B can be contracted in the thickness direction and expanded in the lengthwise direction by, for example, attaching an electrode on each side of a plate-shaped body and applying a voltage to it. Further, this EPAM can change its strain amount, for example, in proportion to approximately square of the voltage applied.

When used as the angular actuator 27a, the EPAM may be formed into a wire shape to expand one side thereof and contract the other side thereby bending the bending portion 27 in a similar manner as the typical function achieved by a wire. Further, such expansion or contraction makes it possible to vary the rigidity thereof, and such a function is utilized in the rigidity varying actuators 54A, 54B to make the rigidity of that portion variable.

Moreover, inside the insertion portion 21, an air/water feed conduit 60a and a suction conduit 61a are inserted, and the rear end thereof provides the connector portion 51 which opens up in the vicinity of the front end of the operation portion 22. And to this connector portion 51, the connector portion 52 provided at the base end of the tube unit 19 is detachably connected.

Further, the air supply/water supply conduit 60a is connected to the air supply/water supply conduit 60b inserted in the tube unit 19, and the suction conduit 61a is connected to the suction conduit 61b inserted in the tube unit 19 and is branched inside the connector portion 52, opening up outside and coming into communication with an inserting port (also referred to as a forceps port) 62. This forceps port 62 is to be closed with a forceps plug 62a when it is not in use.

The rear ends of these air/water feed conduit 60b and the suction conduit 61b provide an air/water supply mouth 63 and a suction mouth 64 in the scope connector 41. The air supply/water supply mouth 63 and the suction mouth 64 are connected to the air supply/water supply mouth and the suction mouth of the AWS adaptor 42 shown in FIG. 3 respectively. Then, inside the AWS adaptor 42, the air/water supply mouth is branched off into an air feed conduit and a water feed conduit, and the air feed conduit is connected to an air feed pump 65 inside the AWS unit 4 through an electromagnetic valve B1, and the water feed conduit is connected to a water feed tank 48. Also, this water feed tank 48 is also connected to the air feed pump 65 via an electromagnetic valve B2 provided at some middle point.

The air feed pump 65, and electromagnetic valves B1 and B2 are connected to the AWS control unit 66 through a control line (drive line), and the opening and closing thereof are controlled by this AWS control unit 66 thereby performing air feed and water feed. The AWS control unit 66 also performs operational control of suction through the opening and closing control of a pinch valve 45.

As shown in FIGS. 1 and 2, the operation portion 22 of the endoscope body 18 is provided with a grip portion 68 for the operator grasping it. In this embodiment, as shown in FIG. 1, this grip portion 68 is formed of a side portion of, for example, a cylindrical body in the vicinity of the rear end (base end) of the operation portion 22 (opposite to the insertion portion 21).

In this grip portion 68, for example, three scope switches SW1, SW2, and SW3 which perform remote control operations such as releasing and freezing are provided along the longitudinal axis in the peripheral portion including the grip portion 68 and are connected to each control circuit 57 (FIG. 2) respectively.

Moreover, the base end surface (normally, as shown in FIG. 1 or FIG. 2, since the base end side is set in upward direction when used for the endoscope inspection, the base end surface is referred to as an upper end surface) provided at the rear end (base end) of the grip portion 68 (or operation portion 22) is configured to be an inclined surface and, on the inclined surface opposite to the position where the scope switches SW1, SW2, and SW3 are provided, there is provided a track ball 69 which has a water tight structure and performs angle operation (bending operation) and the setting of other remote control operations switching from the angle operation. The water-tight structure of this case is actually configured such that the encoder section for rotatably holding the trackball 69 or detecting the amount of rotation thereof is enclosed with a water tight membrane and the trackball 69 is rotatably supported outside thereof.

On the both sides of the trackball 69 on the above described inclined surface, the air/water supply switch SW4 and the suction switch SW5 are disposed in a left-right symmetry relation. This trackball 69 and the scope switches SW4 and SW5 are also connected to the control circuit 57.

Further, as shown in FIG. 2, the endoscope 3 of the present embodiment is provided with an antenna portion 141, for example, inside the operation portion 22 near its rear end so that transmit/receive of the signal data can be performed through the antenna portion 141, and also provided with a battery 151, and a charging circuit 152 and non-contact charging coil 153 connected thereto in the operation portion 22 are also provided.

Accordingly, the connector portion 51 of the operation portion 22 of the present embodiment is formed only of a conduit connector portion which comprises an air/water supply connector and a suction connector.

Thus, the tube unit 19 detachably connected to the endoscope body 18 of the present embodiment eliminates the need of the insertion of signal lines, which is needed for an existing universal cable, and has a structure in which only the conduit tubes of the air/water feed conduit 60b and the suction conduit 61b are inserted.

The above described battery 151 is constructed of a rechargeable secondary battery such as a lithium battery, and this battery 151 is connected to the non-contact charging coil 153, which is incorporated in a portion near the outer surface of the operation portion 22 and has a water-tight structure, via the charging circuit 152. Then a non-contact power supply coil (not shown) provided in an exterior charging apparatus is disposed in opposition to the outer surface of the portion in which the non-contact charging coil 153 is incorporated so that the battery 151 can be charged by applying alternate current to the non-contact power supply coil. Further, as the exterior charging apparatus, a charging apparatus 165 comprising a non-contact power supply coil 184 in the embodiment 2 described later can be adopted.

That is, by applying alternating current to a non-contact power supply coil disposed on the outer surface of the operation portion 22, it is possible to transmit alternating power in a non-contact fashion through electromagnetic coupling to the non-contact charging coil 153 inside the operation portion 22. This alternating power is further transferred to a dc voltage for charging the battery 151 through the charging circuit 152 and is supplied to the battery 151 thereby charging it.

In the present embodiment, since LED 56 is adopted as the illumination means, it is possible to significantly reduce power consumption than in the case where a lamp is used, and also since an ultra high resolution CCD 25 (incorporating a variable gain function) is adopted as the image pickup element, it is possible to obtain a bright image with a good signal/noise ratio even in a condition where the illumination light amount is small. For this reason, even in a case where the battery 151 is adopted, it is possible to perform endoscope inspection for much longer hours compared with prior art cases. Further, it is also possible to adopt a more compact and lighter battery compared with prior art embodiments thereby reducing the weight of the operation portion 22 and ensuring good operability.

According to the present embodiment, the tube unit 19 is constructed only of conduit system thus providing a more suitable configuration for disposable type applications. Moreover, upon recycling (reuse), it is easy to recycle it because there is no electric wire in the tube unit 19.

Moreover, according to the present embodiment, it is possible to use the endoscope with the tube unit 19 detached from the endoscope body 18 when the conduit system is not used. That is, in this case, since the need of the tube unit 19 can be eliminated, it is possible to resolve a case in which the tube unit 19 hinders the operation, thereby improving the operability. Moreover, since the conduit system of the endoscope body 18 can be shortened, it is possible to perform cleaning etc. in shorter hours.

Thus, one of the characteristics of the endoscope 3 of the present embodiment is that the endoscope body 18 is configured to be detachably connected with the tube unit 19 into which only conduit system is inserted, thereby improving the operability and cleanability.

Figure 4:
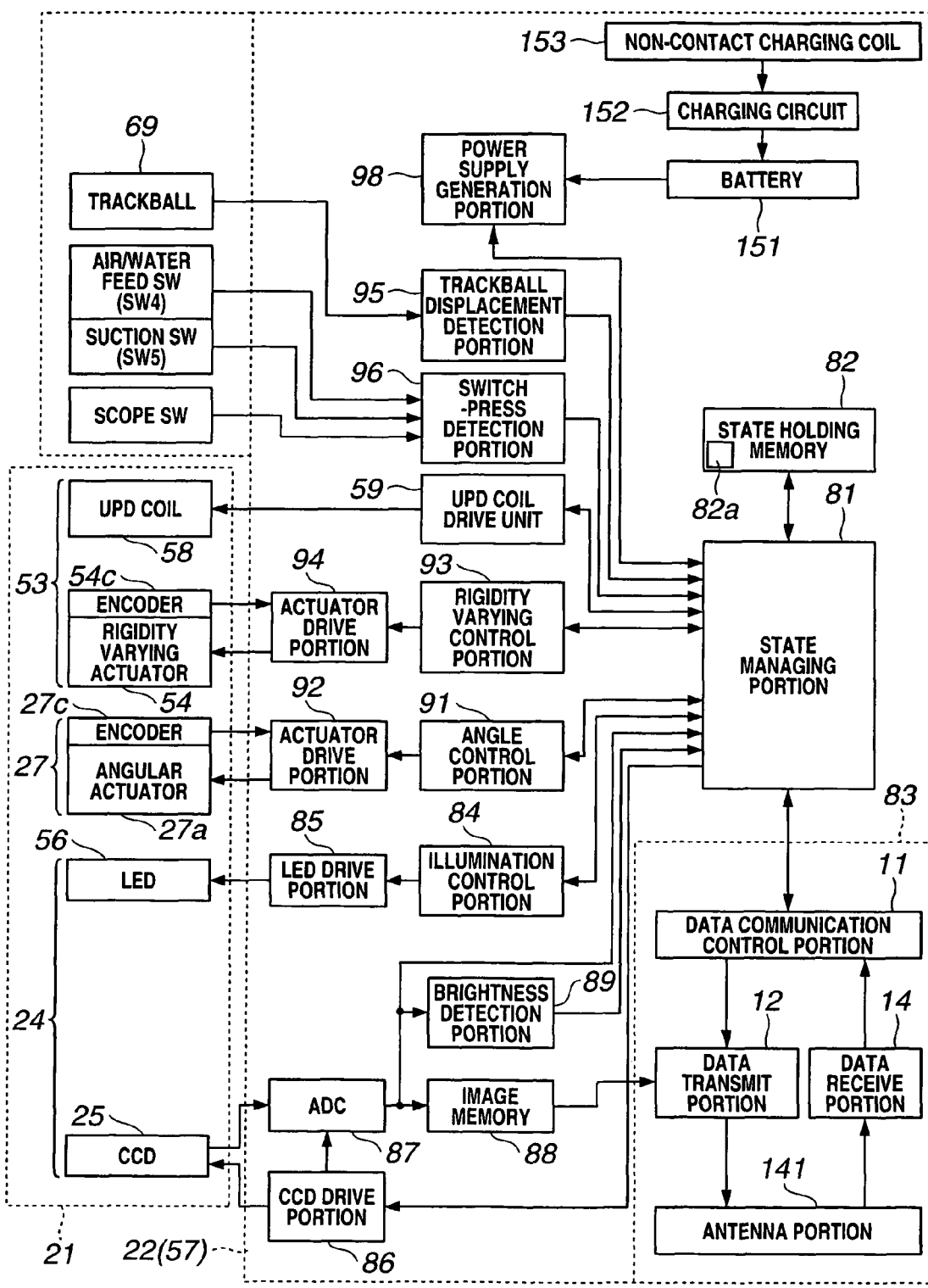
FIG. 4 is a block diagram to show the configuration of electric system in the components provided in the endoscope.

FIG. 4 shows the configuration of the electric systems in the control circuit 57 and others disposed in the operation portion 22 of the endoscope body 18 and in the major components disposed at each portion of the insertion portion 21.

In the tip end 24 of the insertion portion 21 shown in the left bottom portion of FIG. 4, the CCD 25 and the LED 56 are disposed and, in the bending portion 27 shown above it in the figure, the angle actuator (in this embodiment, specifically an EPAM) 27a and an encoder 27c are disposed.

Also, in the flexible portion 53, a rigidity varying actuator 54 (which is, in this embodiment, specifically the rigidity varying actuators 54A and 54B, but is represented by one of them for simplicity) and an encoder 54c are disposed respectively. Further, in this flexible portion 53, the UPD coil 58 is disposed.

Furthermore, on the surface of the operation portion 22 illustrated above the flexible portion 53 of the insertion portion 21, a trackball 69, an air/water supply switch (SW4), a suction switch (SW5), and scope switches (SW1 to SW3) are disposed. Further, as described later, the trackball 69 is used for the angular operation as well as the selection and setting of other functions.

Each circuit of the insertion portion shown in the left portion of FIG. 4 is connected to the control circuit 57 provided in the operation portion 22 (here, the UPD coil drive unit 59 is in the operation portion 22) shown on the right side with respect to the signal line. This control circuit 57 performs drive control of each function and signal processing, etc.

The above described control circuit 57 comprises a state managing portion 81 comprising a CPU managing the control states and others, and this state managing portion 81 is connected to a state holding memory 82 for holding (storing) the state of each portion. This state holding memory 82 has a program storing memory 82a as control information storing means so that even when the components shown in FIG. 4 are modified, (the CPU constituting) the state managing portion 81 can perform control (management) corresponding to the modified configuration by rewriting the program data as the control information, stored in the program storing memory 82a.

Moreover, this state holding memory 82 or at least the program storing memory 82a is comprised of, for example, a non-volatile and electrically rewritable flash memory or EEPROM etc. so that the program data can be readily modified through the state managing portion 81.

For example, it is configured such that the program data can be changed by sending a command of changing the program data through the wireless transmit/receive unit 83 to the state managing portion 81 and, after the command, transmitting the program data to be rewritten from the endoscope system control apparatus 5. Moreover, version upgrading etc. may be readily carried out through the transmit/receive unit 83.

Furthermore, the model information peculiar to each endoscope 3 and individual information corresponding to the state of usage may be written into and held in the state holding memory 82 so that those information can be effectively used. Specifically, the state holding memory 82 may hold, for example, the model information of the endoscope 3 (for example, information such as the kind of CCD 25 and the length of the insertion portion) as well as individual information of each endoscope 3 (for example, usage time (total or cumulative usage hours of endoscope inspection), number of cleaning, adjustment values, maintenance history, etc) which will vary depending on the usage status such as endoscope inspection, and these information will be utilized for decision of the system operation and information provision for users.

Moreover, it is made possible to edit these information from outside such as from the endoscope system control apparatus 5 and a cleaning apparatus not shown.

By doing so, it is possible to share and utilize the state holding memory 82 by making it also perform the function of conventional scope ID, thereby effectively utilizing the information (data) which the scope ID includes. Moreover, since this state holding memory 82 is shared, there is no need to provide a scope ID separately, and it is possible to obtain a higher functionality than that of existing scope ID, and thus to perform more specific and appropriate settings, adjustments, management, processing, etc.

Furthermore, this state managing portion 81 is connected with the wireless transmit/receive unit 83 which communicates based on wireless scheme with the AWS unit 4 (in this embodiment) and the endoscope system control apparatus 5 respectively. This transmit/receive unit 83 is connected with the state managing portion 81 and comprises a data communication control portion 11 for controlling data communication, a data transmit portion 12 for transmitting data, a data receive portion 14 for receiving data, and an antenna portion 141 for transmitting modulated data from the data transmit portion 12 or receiving the data transmitted from the outside by wireless communication.

Moreover, although one transmit/receive unit 83 is shown in FIG. 4, this endoscope 3 is, for example, configured to be able to carry out transmit/receive through up to 4 channels.

In the present embodiment, when data is transmitted based on wireless scheme, for example, according to IEEE802.11g standard, a wireless LAN of a maximum data communication rate of 54 Mbps is formed.

Further, this state managing portion 81 controls a LED drive portion 85 which is controlled by an illumination control portion 84 for controlling illumination, via the illumination control portion 84, and the LED drive portion 85 applies a LED drive signal to the LED 56 to cause the LED 56 which provides illumination means to emit light.

An object such as an affected part, which is illuminated through the light emission by the LED 56, forms an image on the image pickup surface of the CCD 25 disposed at the image forming position through an object lens, which is not shown and attached to the observation window, and the image is subjected to photoelectric conversion.

This CCD 25 outputs signal charges, which are accumulated through photoelectric conversion by the application of a CCD drive signal from the CCD drive portion 86 controlled by the state managing portion 81, as an image pickup signal. This image pickup signal is converted from an analog signal to a digital signal through an A/D converter (abbreviated as ADC) 87 thereafter being inputted to the state managing portion 81, and the digital signal (image data) is stored in an image memory 88. The image data of the image memory 88 are sent to the data transmit portion 12 of the transmit/receive unit 83.

Then, the image data are transmitted from the antenna portion 141 to the endoscope system control apparatus 5 through wireless communication. Moreover, in the case of operations by the air/water supply switch SW4 and the suction switch SW5, the state managing portion 81 performs transmission to the AWS unit 4 through wireless communication via the transmit/receive unit 83.

The output signal of the above described ADC 87 is sent to a brightness detection portion 89 and the information of the image brightness detected by the brightness detection portion 89 is sent to the state managing portion 81. The state managing portion 81 performs light modulation control through the illumination control portion 84 so that the illumination light amount by the LED 56 is of an appropriate brightness level.

The above described state managing portion 81 controls an actuator drive portion 92 through the angle control portion 91, and manages the driving of the angular actuator (EPAM) 27*a* through the actuator drive portion 92. Moreover, the drive amount of the angular actuator (EPAM) 27*a* is detected by the encoder 27*c* and the drive amount is controlled to match the specified value.

Moreover, the state managing portion 81 controls an actuator drive portion 94 through a rigidity varying control portion 93 and performs the management of driving the rigidity varying actuator 54 through this actuator drive portion 94. The drive amount of the rigidity varying actuator 54 is detected by the encoder 54*c* and the drive amount is controlled to match the value corresponding to a specified value. To the state managing portion 81, an operation signal corresponding to the operation amount from the trackball 69 provided in the operation portion 22 is inputted through a trackball displacement detection portion 95.

Further, switch-press operations such as ON operations through the air/water supply switch SW4, the suction switch SW5, and scope switches SW1 to SW3 are detected by a switch-press detection portion 96, and those detected information are inputted into the state managing portion 81. An EPAM has a characteristic to generate an electromotive force by being deformed through an external force, and an EPAM disposed opposite to the EPAM to be driven may be used as the encoder.

In the present embodiment, as described above, there is provided in the operation portion 22, a battery 151, and the charging circuit 152 and the non-contact charging coil 153 connected thereto. Further, this battery 151 is connected to a power supply generation portion 98, and the power supply generation portion 98 provides each portion of the control circuit 57 with a dc voltage necessary for its operation by converting from the dc power supply from the battery 151. Also, this power supply generation portion 98 is connected with the state managing portion 81 and the state managing portion 81 monitors the electrical energy state (for example, a remaining amount of electrical energy) of the battery 151 by monitoring the power supply state of the power supply generation portion 98.

Figure 6A:
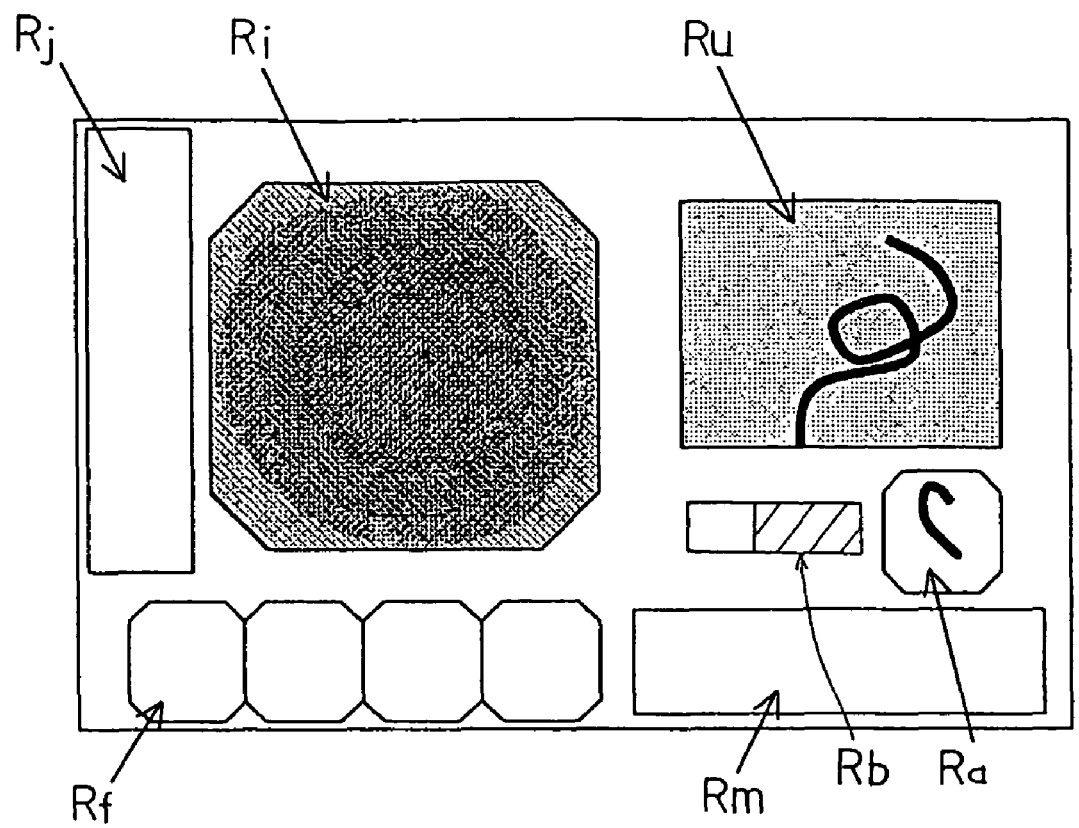
FIG. 6A is an explanatory diagram to show a typical display example of the monitor display surface of an observation monitor.

Then, the detected electrical energy state of the battery 151 is sent from the transmit/receive unit 83 to the endoscope system control apparatus 5 to display the remaining amount of the electrical energy of the battery 151 on the observation monitor 6 as shown in FIG. 6A. Furthermore, in stead of the continuous display as shown in FIG. 6A, a state in which the electrical energy of the battery 151 has decreased below a predetermined value may be displayed on the observation monitor 6 when the remaining amount of the electrical energy of the battery 151 is detected to have declined below the predetermined value.

Figure 5:
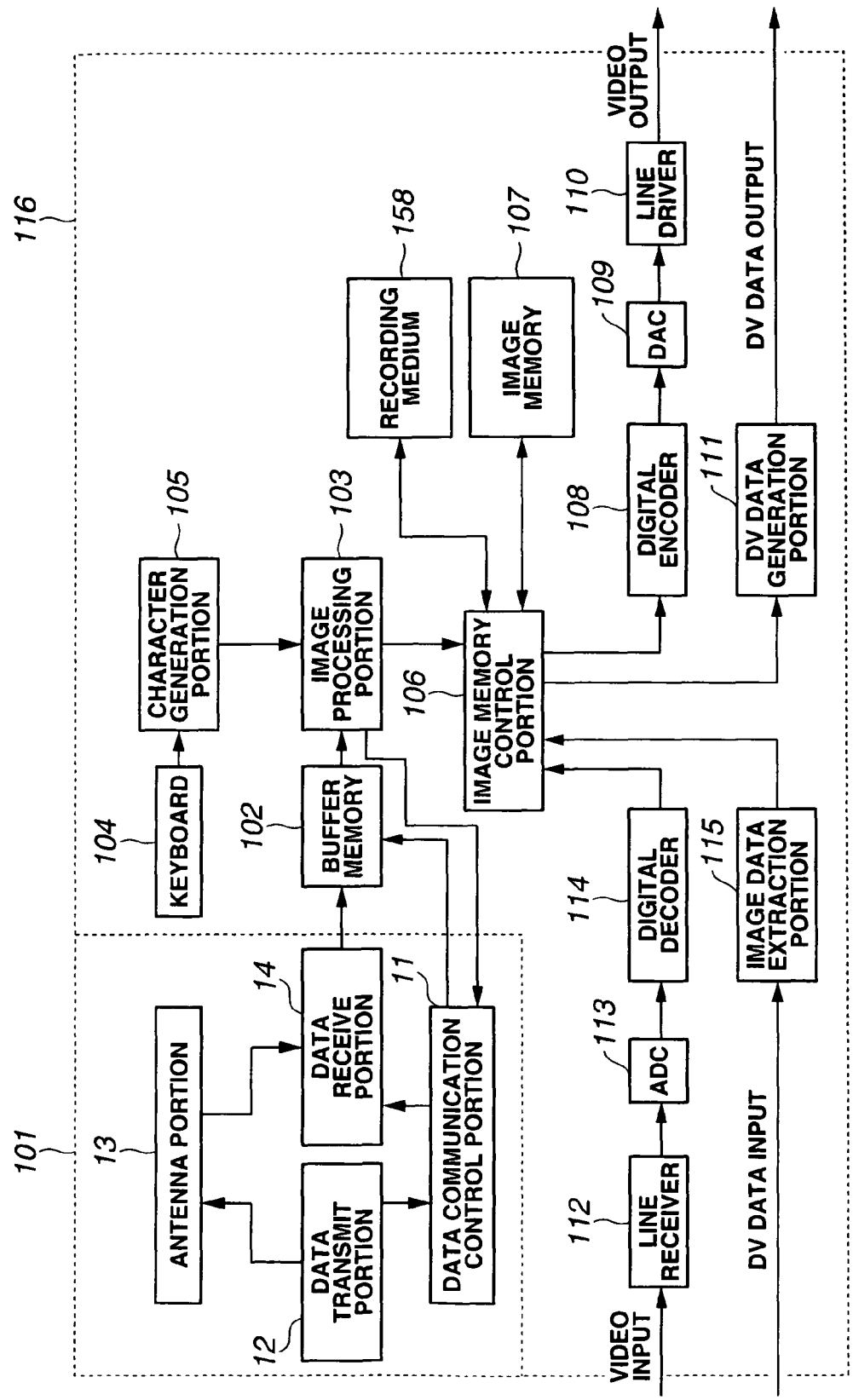
FIG. 5 is a block diagram to show the configuration of the electrical systems in the major portions of the endoscope system control apparatus.

FIG. 5 shows the interior configuration of the transmit/receive unit 101 and the image processing unit 116 in the endoscope system control apparatus 5 of FIG. 3. This endoscope system control apparatus 5 has, for example, a transmit/receive unit 101 based on a wireless scheme. The data such as image signals transmitted based on wireless scheme from the AWS unit 4 are acquired by an antenna portion 13 and sent to the data receive portion 14, amplified, and thereafter demodulated. The operation of this data receive portion 14 is controlled by the data communication control portion 11 so that the received data are successively accumulated in a buffer memory 102.

The image data of this buffer memory 102 are sent to an image processing portion 103 for processing the image data. Into this image processing portion 103, besides the image data from the buffer memory 102, character information from a character generation portion 105 which generates character information through the key input from a keyboard 104, is inputted so that character information can be superimposed on the image data.

The image processing portion 103 send the inputted image data etc. to an image memory control portion 106 and, through this image memory control portion 106, temporarily stores the image data etc. in an image memory 107 and records them in a recording medium 158. The above described image memory control portion 106 reads the image data temporally stored in the image memory 107 and sends them to a digital encoder 108, and the digital encoder 108 encodes the image data into a video format and output them to a D/A converter (abbreviated as DAC) 109. This DAC 109 converts the digital video signal to an analog video signal. This analog video signal is further passed through a line driver 110 and outputted from a video output terminal to the observation monitor 6, so that an image corresponding to the video signal is displayed on the observation monitor 6.

Further, the image data temporally stored in the image memory 107 are read out and inputted to a DV data generation portion 111, and DV data are generated by this DV data generation portion 111 and the DV data are outputted from the DV data output terminal.

Furthermore, this endoscope system control apparatus 5 is provided with a video data input terminal and a DV data input terminal, the video signal inputted from the video input terminal passed through a line receiver 112 and an ADC 113, and the video signal converted to a digital signal is demodulated by a digital decoder 114 and inputted to the image memory control portion 106.

Further, with regard to the DV data inputted to the DV data input terminal, image data are extracted (decoded) by an image extraction portion 115 and inputted to the image memory control portion 106.

Also, for the video signal (image data) inputted from the video input terminal or DV data input terminal, the image memory control portion 106 temporarily records them into the image memory 107, or records them in a recording medium 158, or outputs them from the video output terminal to the observation monitor 6.

In the present embodiment, image data picked up by the CCD 25 of the endoscope 3 and the UPD image data generated by the UPD unit 76 from the AWS unit 4 are inputted through wireless transmission into the endoscope system control apparatus 5, and the endoscope system control apparatus 5 converts those image data into a predetermined video signal to output it to the observation monitor 6. Moreover, the endoscope system control apparatus 5 may receive the UPD coil position data instead of the UPD image data, and generate the UPD image data in the image processing portion 103.

In the endoscope system 1 comprising the present embodiment, upon turning on the power, various images for example as shown in FIG. 6A are displayed on the observation monitor 6.

In this case, an information display area Rj for displaying patient information etc., an endoscope image display area Ri, a UPD image display area Ru, a freeze image display area Rf, an angular shape display area Ra, a remaining amount display area Rb for displaying the remaining amount of electrical energy of the battery 151, as well as a menu display area Rm are provided, and menus are displayed in the menu display area Rm.

Moreover, the angular shape display area Ra detects the angular operation amount of the angular actuator 27a through the encoder 27c and displays the angular shape in that case.

Figure 6B:
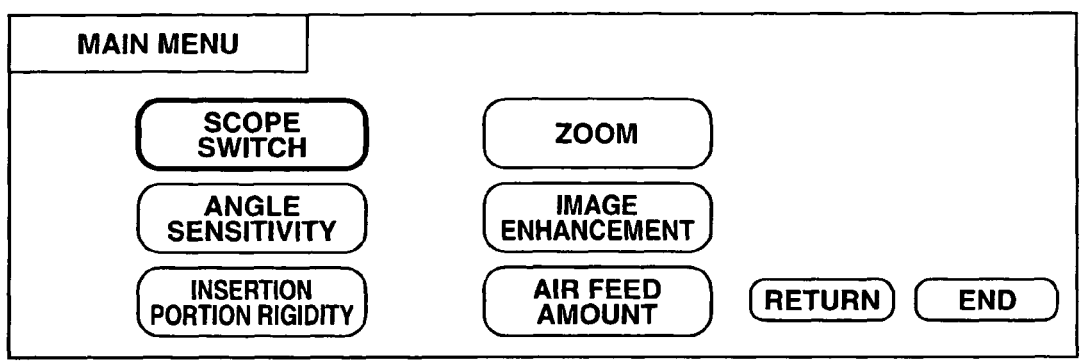
FIG. 6B is an explanatory diagram to show a display example of a main menu.

The menu displayed in the menu display area Rm includes main menus shown in FIG. 6B. On this main menu, scope switch, angle sensitivity, insertion portion rigidity, zoom, image enhancement, air supply amount as well as "Return" which instructs the operation of returning to the previous screen, and "End" which instructs the end of the menu are displayed.

Figure 6C:
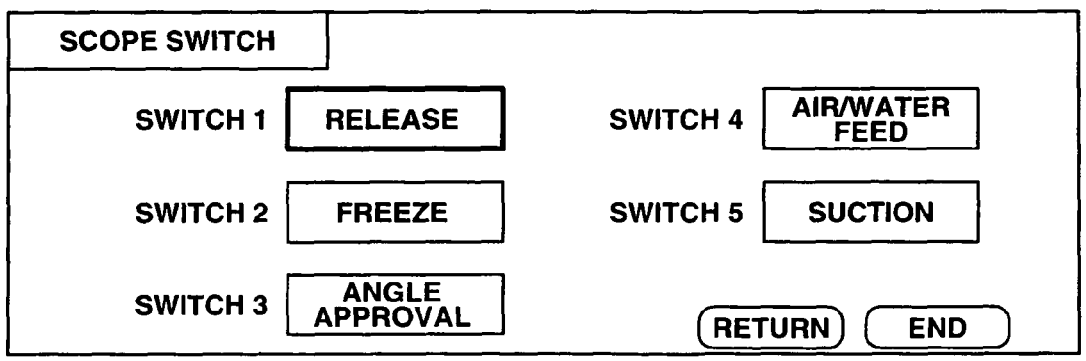
FIG. 6C is an explanatory diagram to show a display example of a function selection menu.

Then, when a user moves a selection-frame to an item of the scope switch to be selected through the operation of trackball 69 etc., the frame for the item of the scope switch will be displayed in a thick line indicating the selection, and when a decision operation is further performed by pressing down the trackball 69, the function to be designated to each of 5 scope switches SW1 to SW5 can be selected and set as shown in FIG. 6C.

Next, the action of the endoscope system 1 configured as described so far will be described.

As the preparation for performing endoscope inspection, first the connector portion 52 on the tube unit 19 of a disposable type is connected to the connector portion 51 of the operation portion 22 of the endoscope body 18, thereby completing the preparation of the endoscope 3.

Next, the scope connector 41 of the tube unit 19 is connected to the connector 43 of the AWS unit 4. By one-touch connection for this part, the connection of various conduits is completed by one connection operation. There is no need of performing the connection of various conduits and electric connectors each time individually as in the case of a conventional endoscope system. Moreover, the connector 43 of the AWS unit 4 is configured such that when besides an endoscope 3 having no power supply line (of the tube unit 19) such as the present embodiment, an endoscope (not shown) (comprising a tube unit 19) having a power supply line etc. is connected, power supply and signal transmission can be performed.

Further, the user will connect the AWS unit 4 to the UPD coil unit 8 thereby connecting the endoscope system control apparatus 5 to the observation monitor 6. Furthermore, by connecting the endoscope system control apparatus 5 to the image recording unit 7 etc. as needed, the setup of the endoscope system 1 will be completed.

Next, the power supply for the AWS unit 4 and the endoscope system control apparatus 5 are turned on. Further, the power supply switch of the endoscope 3 is turned ON. This power supply switch is activated by keeping the scope switches SW4 and SW5 being pressed simultaneously for a predetermined time.

Then, each portion in the endoscope 3, the AWS unit 4, and the endoscope system control apparatus 5 are brought into an operation state.

Figure 7:
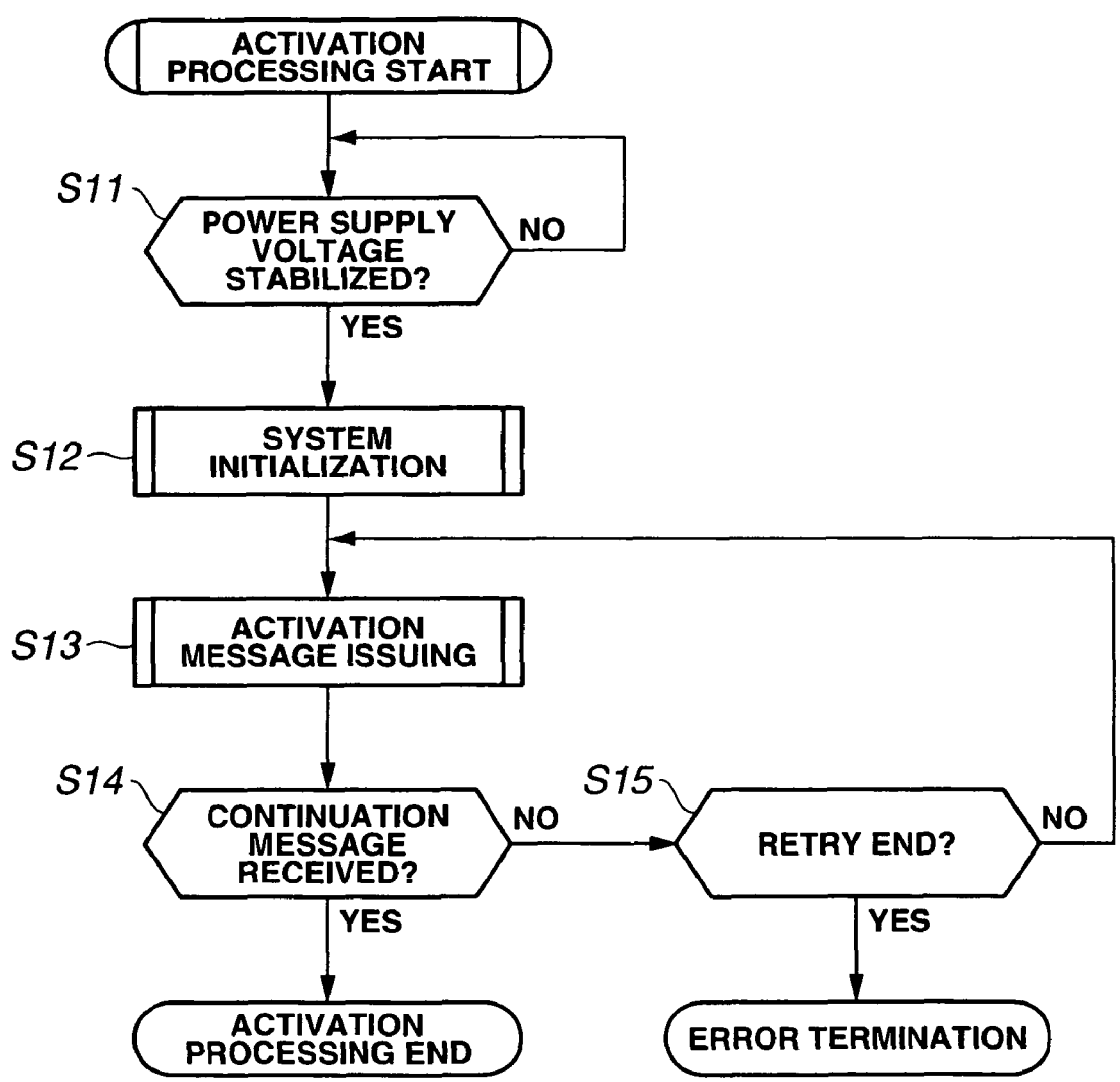
FIG. 7 is a flowchart to show the operation contents of the activation processing of the endoscope system control apparatus.

In such a case as described above, the operations during the activation of the endoscope 3 are as shown in FIG. 7.

In the endoscope 3, the power supply generation portion 98 supplies each portion of the control circuit 57 with power of a voltage needed for the operation thereof through the dc power from the battery 151, and the state managing portion 81 of the control circuit 57 starts the activation processing. Then, in the first step S11, the state managing portion 81 waits for the power supply voltage of the power supply generation portion 98 to be stabilized as shown in FIG. 7.

Then, when the power supply voltage is stabilized, the state managing portion 81 performs the initialization of each portion of the control circuit 57 in the next step S12. After this system initialization, the state managing portion 81 transmits an activation message from the transmit/receive unit 83 to the endoscope system control apparatus 5 as shown in step S13.

After the transmission of this activation message, as shown in step S14, the state managing portion 81 comes into a state of waiting for the reception of a continuation message from the endoscope system control apparatus 5, and when receiving a continuation message, it ends the activation processing. On the other hand, when not receiving a continuation message, as shown in step S15, the state managing portion 81 returns to step S13 if the condition for retry completion (for example, a predetermined condition for number of retrys) is not met, and re-issues an activation message, and if the condition for retry completion is met, terminates with an error.

When the above-described activation processing normally ends, image pickup by the CCD 25 is started, and a user can perform air/water supply, suction, angle operation, and rigidity varying operations etc. with the operation means of the operation portion 22.

Figure 8:
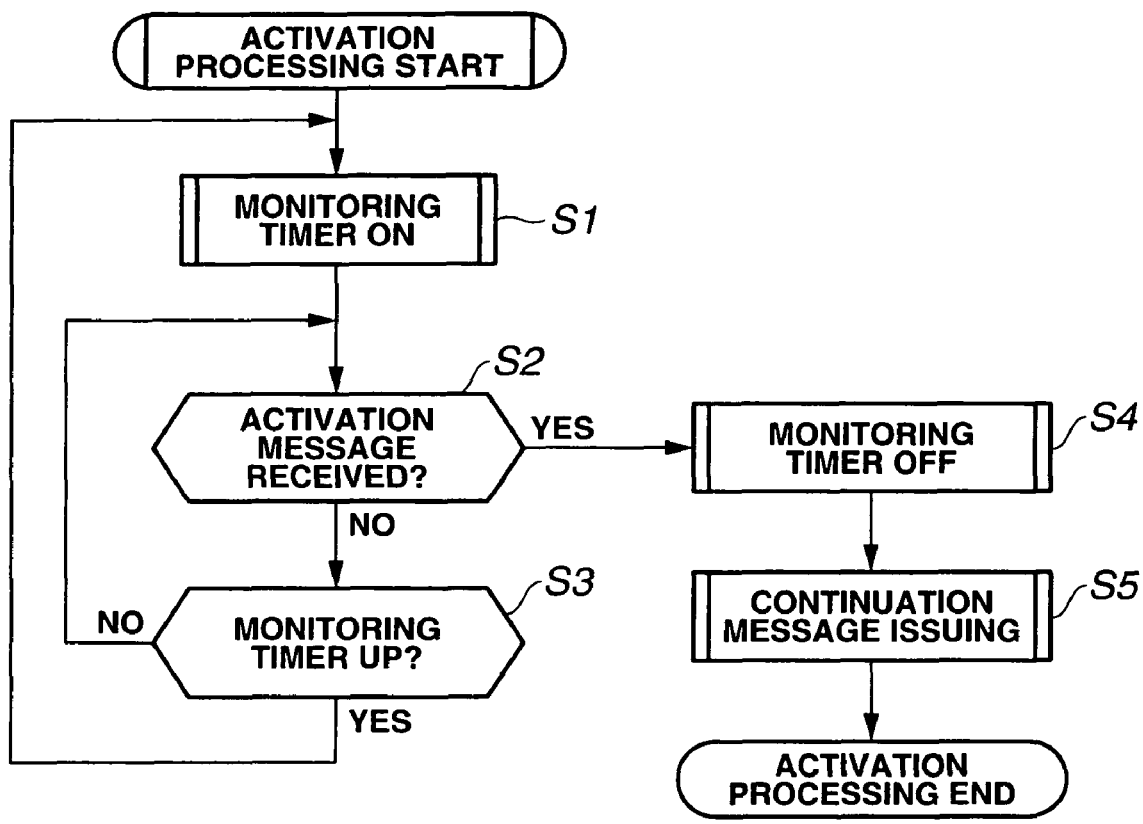
FIG. 8 is a flowchart to show the operation contents of the activation processing of the endoscope.

On the other hand, as shown in FIG. 8, when starting the activation processing, the endoscope system control apparatus 5 comes into a state of waiting for an activation message from the endoscope 3 as shown in step S2 after turning on the monitoring timer in the first step S1. Then, if an activation message is not received, determination on whether or not the monitoring timer is in time-out is made as shown in step S3, and if not in time-out, the process returns to step S2, and if in time-out, the process returns to step S1.

On the other hand, if an activation message is received before time-out at step S2, the time measurement of the monitoring timer is turned off as shown in step S4. Then, a continuation message is issued as shown in step S5 and the activation processing ends.

Further, the UPD image by the AWS unit 4 is also transmitted to the endoscope system control apparatus 5 through wireless communication so that the UPD image is displayed on the observation monitor 6 as shown in FIG. 6A.

Next, as a typical processing operation by the endoscope 3, operation contents of the image pickup control processing according to FIG. 9 will be described.

Figure 9:
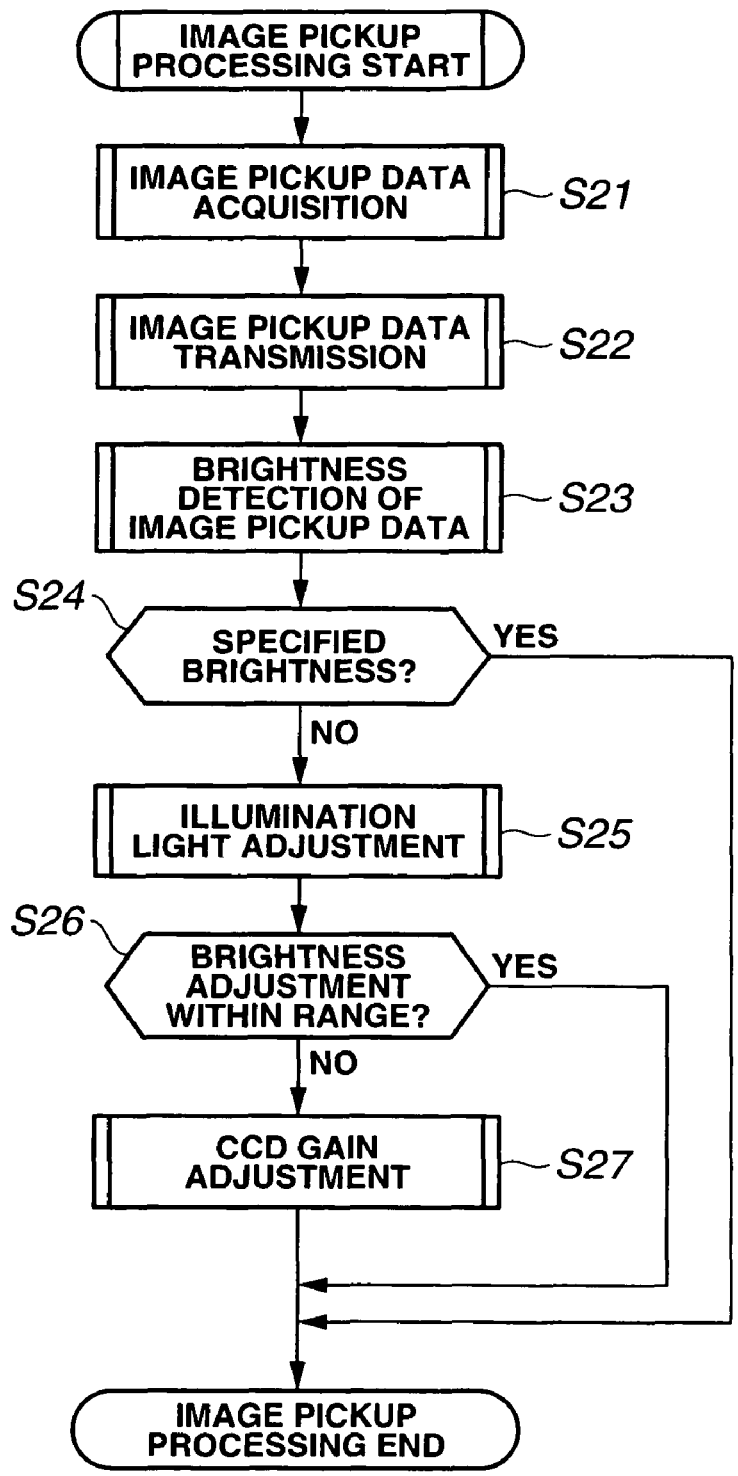
FIG. 9 is a flowchart to show the operation contents of the image pickup control processing.

As shown in FIG. 9, when image pickup processing starts, the endoscope 3 performs the acquisition of image pickup data as shown in step S21. Specifically, under the management (control) of the state managing portion 81, the LED 56 emits light and a CCD drive portion 86 starts the operation of driving the CCD 25, and the image pickup signals picked up by the CCD 25 are converted to digital signals (image pickup data) by an ADC 87. The image pickup data (image data) are sequentially stored in the image memory 88, and the acquisition of the image pickup data is performed.

The acquired image data are sequentially transmitted as shown in step S22. The image data read out from the image memory 88 are transmitted from the transmit/receive unit 83 to the endoscope system control apparatus 5 through wireless communication, and, in the apparatus 5, converted to a video signal to be displayed on the observation monitor 6.

Further, the image pickup data of the ADC 87 are inputted to the brightness detection portion 89. As shown in step S23, this brightness detection portion 89 detects the brightness of the image pickup data such as by calculating an average value for an appropriate time period, of the luminance data for the image pickup data.

The detection data of this brightness detection portion 89 is, for example, inputted to the state managing portion 81 and determination is made on whether or not the brightness is at a specified level (step S24). Then, the brightness is at the specified level, image pickup processing is completed thereby moving to next image pickup processing.

On the other hand, in step S24, if the state managing portion 81 determines that the brightness is not at a specified level, an instruction signal (control signal) of illumination light adjustment is sent to the illumination control portion 84, and the illumination control portion 84 adjusts the illumination light amount. For example, the illumination control portion 84 adjusts the illumination light amount by increasing or decreasing the drive current to cause the LED 56 to emit light. The illumination control portion 84 returns this adjustment result to the state managing portion 81.

Therefore, the state managing portion 81 makes determination on whether the brightness is within the adjustment range in which the illumination control portion 84 can perform, based on the information about the adjustment result. Then, if the brightness adjustment can be performed by the illumination control portion 84, the image pickup processing is brought to an end without performing the processing of step S27. On the other hand, if the brightness adjustment range by the illumination control portion 84 is exceeded, the state managing portion 81 outputs a CCD gain adjustment signal to the CCD drive portion 86 and adjusts the gain of the CCD 25 thereby adjusting the brightness of the image pickup data. Then, the image pickup processing is brought into an end.

According to the endoscope 3 of the present embodiment constituting an endoscope system 1 to perform such operations, since the battery 151, the charging circuit 152, and the non-contact charging coil 153 are disposed inside the exterior body of a water tight structure of the operation portion 22 so that the battery 151 can be charged in a non-contact fashion and there is no electrical contact exposed on the outer surface of the endoscope 3, the endoscope can be used without degradation in electrical contacts etc. even if cleaning or sterilization is performed repeatedly.

That is, generally, the endoscope 3 can be used for endoscope inspection through the power of the battery 151. Then, when performing cleaning or sterilization after finishing the endoscope inspection, it is possible to finish it in shorter hours than in the case of an endoscope in which an existing universal cable is integrated, since the cleaning and sterilization can be performed with the conduits being shortened by detaching the tube unit 19. Therefore, according to the present embodiment, it is possible to increase the proportion of usage time used for endoscope inspection thereby increasing the efficiency of usage.

Furthermore, during endoscope inspection, since the remaining amount of electric energy of the battery 151 is displayed on the remaining amount display area Rb as shown in the diagonally shaded area in FIG. 6A on the observation monitor 6, it is possible to keep track of the level of consumption of electrical energy of the battery 151. Moreover, the remaining amount of electrical energy may be displayed in usable hours in normal usage conditions.

Further, by using the battery 151, it is made possible to eliminate the need of inserting a power supply line thereby simplifying the structure of the tube unit 19.

Moreover, by making the endoscope 3 to be separable at the operation portion 22 into the endoscope body 18 and the tube unit 19 and making the tube unit 19 to be disposable, it is made possible to perform the cleaning and sterilization of the endoscope body 18 with ease.

That is, the air/water feed conduit 60a and the suction conduit 61a of the endoscope body 18 can be constructed much shorter in length than a conventional example in which a universal cable corresponding to the tube unit 19 is integrally formed, and therefore the cleaning and sterilization thereof can be performed much easier.

Moreover, in this respect, although in the case of the convention example in which the universal cable corresponding to the tube unit 19 is integrally formed, the operation portion 22 is consecutively installed in such a way that the universal cable is bent from the operation portion 22, in the case of the present embodiment, the operation portion 22 has a connector portion 51 which is slightly bent at the connector portion 51, but other portions of the air/water feed conduit 60a and the suction conduit 61a are configured to be nearly straight, cleaning and sterilization of the interior of the conduits can be performed easily and in short hours. Therefore, it is possible to set up an endoscope inspection ready in a shorter period of time.

Further, in the present embodiment, since the endoscope body 18 and the tube unit 19 are configured to be separable, it is possible to use the endoscope body 18 alone when air/water supply and suction operations are not performed, and in such a case, there is no need of routing the tube unit 19 from the vicinity of the operation portion 22, thereby significantly improving the operability.

That is, according to the present embodiment, it is made possible to use the endoscope body 18 alone depending on the use environment. Therefore, for example, it becomes possible to carry this endoscope body 18 out on the road and use it outside the hospital, etc.

Moreover, the present embodiment is configured such that the operation portion 22 is provided with numerous operation means such as angle operation means, air/water supply means, suction means, rigidity varying means, freeze operation means, and release operation means; and these operation means are intensively (collectively) controlled by the control circuit 57 provided in the operation portion 22. Further, this control circuit 57 is configured to intensively control the light emitting means for projecting illumination light for performing image pickup and the image pickup means for picking up images, as well as the above-described operation means.

Moreover, since the present invention is configured such that various functions provided in the endoscope body 18 are intensively controlled by the control circuit 57 provided in the operation portion 22, and also various functions of the operation means for the AWS unit 4 and the endoscope system control apparatus 5 as well are intensively controlled, the user (more specifically the operator) can freely perform various operations through various operation means provided in the operation portion 22, and thus the operability is significantly improved.

In particular, since the present embodiment is configured such that a control circuit 57 for performing intensive control is provided in the operation portion 22 so that the image data picked up by the CCD 25 and various signals by the operation means are transmitted in a packet from the control circuit 57 to the AWS unit 4 and the endoscope system control apparatus 5 through wireless communication, it is possible to eliminate the need of an electrical signal line.

Therefore, it is possible to eliminate the need of inserting a signal line in the tube unit 19 connected at the connection portion of the operation portion 22, thereby allowing a disposal configuration of the tube unit 19.

Further, since it is not necessary to insert a signal line in the tube unit 19, it is possible to reduce the radius of the tube unit 19 and make it bendable more easily, thereby improving the operability while the user operates it.

Moreover, a variation of the present embodiment may have a structure in which for example a recess portion (such as in the next embodiment 2) is provided in the outer surface of the operation portion 22 opposite to the non-contact charging coil 153 so that a non-contact charging coil in the charging apparatus for supplying ac power in a non-contact fashion (to the non-contact charging coil 153) can be mounted in that recess portion.

Figure 10:
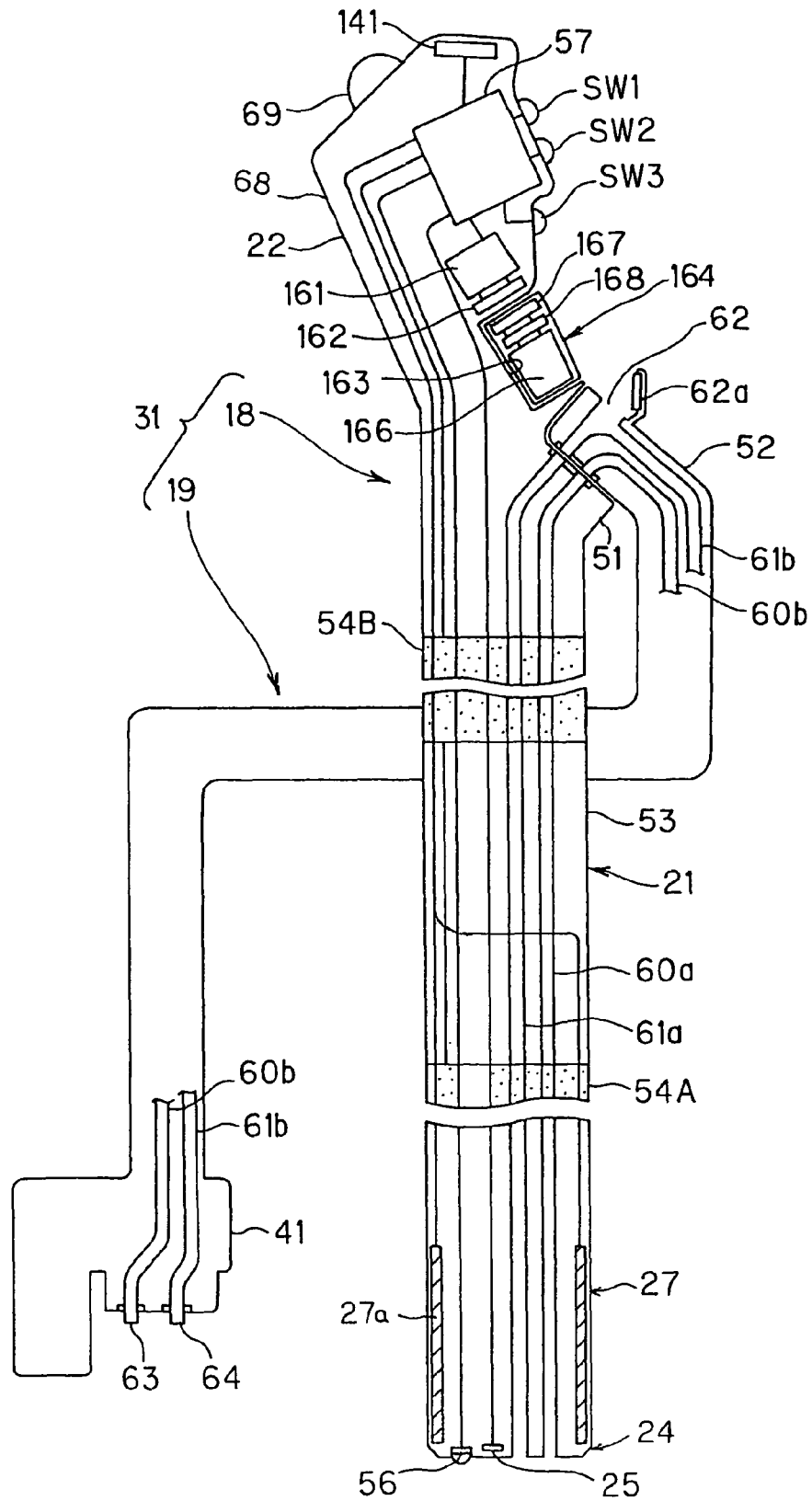
FIG. 10 shows the general configuration of the endoscope according to the second embodiment of the present invention.
Figure 11A:
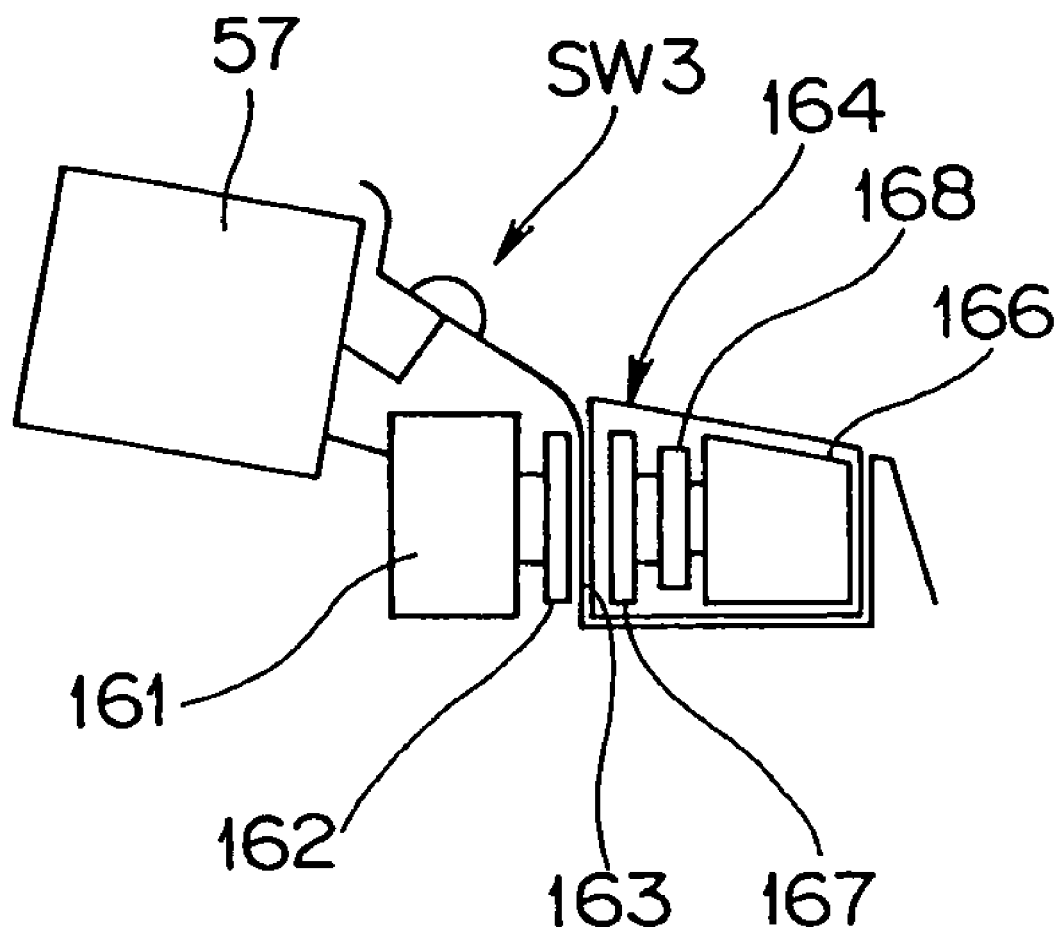
FIG. 11A is an explanatory diagram to show the configuration and the circuit configuration of the peripheral portion of a battery unit.

Next, the embodiment 2 will be described with reference to FIGS. 10 to 11(C). FIG. 10 shows the configuration of the endoscope of the embodiment 2 and FIG. 11(A) shows the configuration of the peripheral portion of the battery unit, etc. As shown in FIG. 10, in the endoscope 31 of the present invention, there is disposed a power supply circuit 161 in stead of the battery 151 and the charging circuit 152 incorporated in the image pickup portion 22 in the endoscope 3 in FIG. 2. Moreover, a non-contact power supply coil 162 is connected to this power supply circuit 161 to provide a structure in which a recess portion 163 is formed at the position opposite to the portion incorporating the non-contact power supply coil 162 in the operation portion 22 so that a non-contact battery unit 164 can be detachably mounted to the recess portion 163.

Figure 11B:
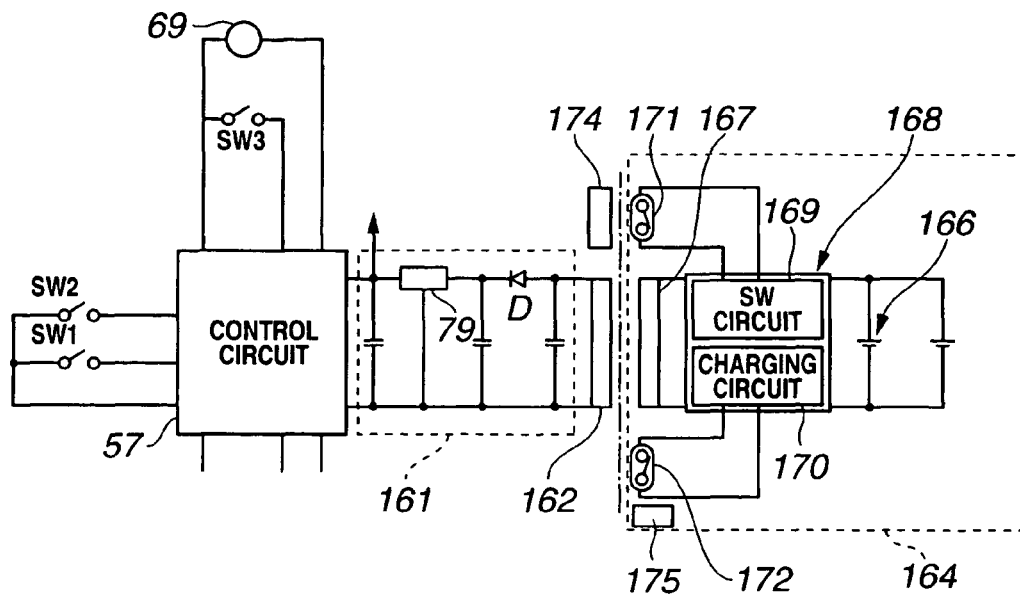
FIG. 11B is a circuit block diagram to show the internal configuration of FIG. 11A.
Figure 11C:
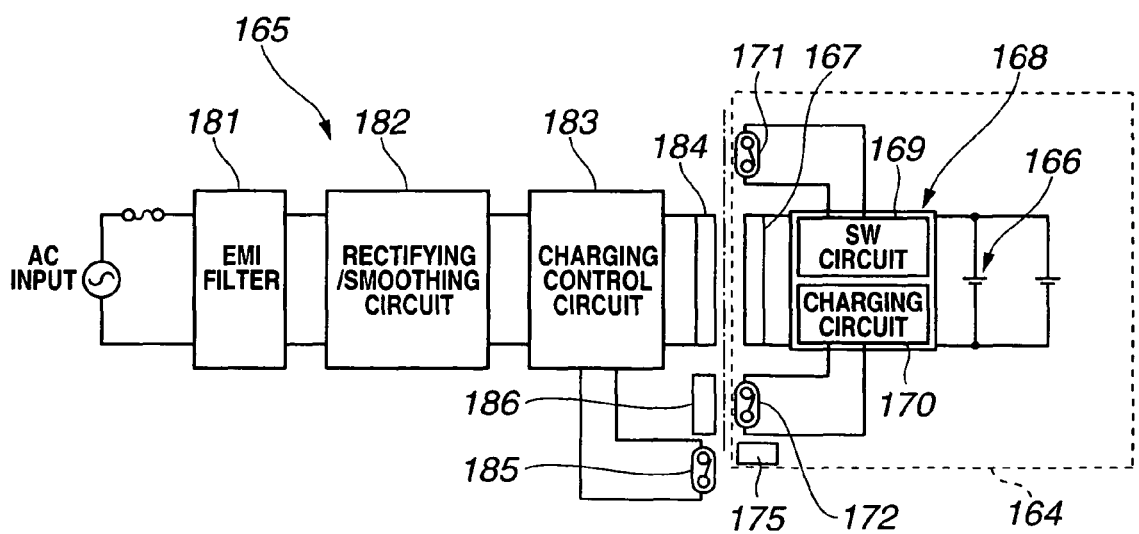
FIG. 11C is a circuit block diagram to show the circuit configuration for charging the battery by a charging apparatus.

FIG. 11A is an enlarged view to show the vicinity of the battery unit 164, FIG. 11B shows the internal configuration in FIG. 11A, and FIG. 11C shows the circuit configuration for charging a battery 166 through a charging apparatus 165 by connecting the battery unit 164 to the charging apparatus 165.

As shown in FIG. 11A, in the battery unit 164 comprising a water-tight exterior case mounted to the recess portion 163 provided in the operation portion 22, a non-contact power supply coil 167 is disposed in a portion in opposition to a non-contact power supply coil 162 on the power supply circuit 161, and this non-contact power supply coil 167 is connected to the battery 166 via a power supply circuit 168. As shown in FIG. 11 B, the non-contact power supply coil 167 is connected to a switching circuit 169 and a charging circuit 170 which constitute the power supply circuit 168, and the switching circuit 169 and the charging circuit 170 are connected respectively with lead switches 171 and 172 as a magneto-sensitive switch for going ON or OFF in response to magnetism (magnetic field). This battery unit 164 is housed in the exterior case and has a waterproof structure (water-tight structure). Moreover, the power supply circuit 161 is connected to the other non-contact power supply coil 162 disposed water-tightly in the operation portion 22 opposite to the recess portion 163, and this power supply circuit 161 is configured as follows. The ac power transmitted to the non-contact power supply coil 162 is rectified by a rectifier diode D, smoothed by being removed of pulsating component through a smoothing condenser, inputted to a three-terminal power supply IC 79, and converted to a predetermined voltage by this three-terminal power supply IC 79.

The dc power of a predetermined voltage generated by this power supply circuit 161 is supplied to each portion of the control circuit 57.

Further, when a magnet 174 is disposed near the portion opposite to the lead switch 171 in the operation portion 22, and the battery unit 164 is mounted to the recess portion 163 as shown in FIG. 11A, the lead switch 171 is turned ON by the magnetism of this magnet 174. On the other hand, a magnet 175 is also disposed on the side of the other lead switch 172, but since this magnet 175 is configured such that the lead switch 172 will not be acted by its magnetism and the magnetic flux is directed toward the side of the lead switch 172, the lead switch 172 will be turned OFF (the magnet 175 is utilized to control the charging apparatus 165 as shown in FIG. 11C).

Accordingly, the power of the battery 166 is supplied to the switching circuit 169, and this switching circuit 169 performs switching operation, and, a pulsed (ac) current switched by this switching operation is transmitted to the non-contact power supply coil 162 magnetically coupled with the non-contact power supply coil 167 in a non-contact fashion through the non-contact power supply coil 167. Then, a dc power of a predetermined voltage is generated by the power supply circuit 161 connected to the non-contact power supply coil 162.

Further, the charging apparatus 165 for charging the battery 166 of this battery unit 164 has a circuit configuration shown in FIG. 11C.

The ac power from the ac power supply is inputted to a rectifying/smoothing circuit 182 through an EMI filter 181 and converted to a smoothed dc power, and thereafter supplied to a charging control circuit 183 which performs switching operation for performing charging control as approximately same manner as the switching circuit 169. There is connected to the output terminal of this charging control circuit 183 a non-contact power supply coil 184 and an ac power switched by the charging control circuit 183 is supplied to the non-contact power supply coil 167 through the non-contact power supply coil 184.

Further, there is connected to the charging control circuit 183 a lead switch 185, and by mounting the battery unit 164 into a recess portion provided in the charging apparatus 165, the lead switch 185 is turned ON in response to the magnetism by the magnet 175 provided on the battery unit 164. Further, it is configured such that the lead switch 172 connected to the charging circuit 170 may be turned ON by the magnet 186 provided on the charging apparatus 165.

Accordingly, in this case, the charging control circuit 183 comes into an operation state and performs switching operation to supply an ac power from the non-contact power supply coil 184 to the non-contact power supply coil 167. The ac power supplied to the non-contact power supply coil 167 is converted to a dc voltage for charging the battery 166 by the charging circuit 170 to charge the battery 166.

Moreover, the charging control circuit 183 monitors the current supplied to the non-contact power supply coil 167 from the non-contact power supply coil 184 and detects the charging state of the battery 166 from the monitored values, and when a predetermined charging state is reached, it stops the supply of ac power to light up a LED (not shown) etc. thereby informing the completion of charging.

Thus, according to the present embodiment, by mounting a detachable battery unit 164 onto the endoscope body 18, it is possible to perform intensive control operations by the control circuit 57 provided in the operation portion 22.

Moreover, when the electric energy of the battery 166 in the battery unit 164 is exhausted or the level of the electric energy is lowered, it is possible to charge this battery 166 in a non-contact fashion by mounting the battery unit 164 onto the charging apparatus 165 as shown in FIG. 11C.

According to the present embodiment, since there is no need to insert an electric signal line in the tube unit 19, it is possible to reduce the cost of the tube unit 19 and realize a tube unit 19 more suitable for a disposable type. Moreover, it is possible to reduce the diameter of the tube unit 19 thereby improving the operability when operating the operation portion 22.

Moreover, as with the embodiment 1, since the endoscope body 18 is configured to be separable from the tube unit 19 in the vicinity of the operation portion 22, it is possible to perform the cleaning and sterilization of the endoscope body 18 in shorter hours. That is, the cleanability and sterilizability are improved.

Further, according to the present embodiment, switching between the charging of the battery 166 and the power supply from the battery 166 to the power supply circuit 161 inside the operation portion 22 can be performed by a simple operation.

That is, it is possible to supply power in a contact-less and non-contact fashion to the power supply circuit 161 through the non-contact power supply coil 162 by turning on the lead switch 171 in association with the operation of mounting the battery unit 164 into the recess portion 163 such that the switching circuit 169 comes into an operation state; on the other hand, it is possible to charge the battery 166 by mounting this battery unit 164 onto the charging apparatus 165 so that the charging circuit 170 is switched into an operation state in association with the mounting operation.

Further, according to the present embodiment, when the air/water supply operation and the suction operation are not necessary, it is also possible to use the endoscope body 18 with the tube unit 19 being detached therefrom as described in the embodiment 1.

Furthermore, in the present embodiment, switching is performed such that power is supplied form the battery 166 of the battery unit 164 to the power supply circuit 161 by mounting the battery unit 164 to the recess portion 163, which may be applied to the embodiment 1.

That is, the switching may be performed such that charging of the battery 151 is started by disposing or mounting the non-contact power supply coil of the charging apparatus to the position (on the outer surface of the operation portion 22) opposite to the non-contact charging coil 153 so that the sate in which the output of the battery 151 is outputted to the power supply generation portion 98 is changed to the state in which charging output of the charging circuit 152 is supplied to the battery 151 by the ac power supplied to the non-contact charging coil 153.

In this case, it may be configured such that while the output of the battery 151 is outputted to the power supply generation portion 98, the operation of charging the battery 151 with charging output of the charging circuit 152 is further performed with the ac power supplied to the non-contact charging coil 153.

Thus, embodiments which are configured by partially combining each of the above described embodiments also belong to the present invention.

Further, variations which are modifications of each embodiment also belong to the present invention. For example, a configuration in which the connection portion of the tube unit 19 is modified, for example, by displacing it from the grip portion 68 or the operation portion 22 toward the base end (rear end) of the insertion portion 21 also belongs to the present invention.

In the present invention, it is obvious that a wide range of different embodiments may be configured based on the present invention without deviating from the spirit and the scope of the present invention. The present invention will not be limited by specific embodiments except as they may be limited by the appended claims.

What is claimed is:

1. An endoscope comprising:
an elongated insertion portion;
an operation portion provided at the rear end of the insertion portion;
a contact-less endoscope exterior body, wherein no electrical contact is exposed on the outer surface of the endoscope exterior body including the insertion portion and the operation portion;
an image pickup apparatus disposed inside the endoscope exterior body and for performing image pickup, and a signal processing portion for performing signal processing for the image pickup apparatus;
a battery of a water-tight structure for supplying power to at least the image pickup apparatus and the signal processing portion;
a charging apparatus of a water-tight structure for charging the battery with power supplied in a contact-less fashion, and
a switching portion for switching between a state of supplying the power of the battery to the image pickup apparatus and the signal processing portion and a state of charging the battery through the charging apparatus.

2. The endoscope according to claim 1, wherein the battery and the charging apparatus are disposed inside a peripheral portion of the endoscope exterior body having a water-tight structure, the peripheral portion including the operation portion.

3. The endoscope according to claim 1, wherein the battery and the charging apparatus are provided in a housing of a water-tight structure which is configured to be detachably mounted to a peripheral portion including the operation portion in the endoscope exterior body having a water-tight structure.

4. The endoscope according to claim 3, characterized in that the housing incorporates a power supply portion for converting a dc power from the battery to an ac power, and supplying the dc power in a contact-less fashion to the outside of the housing.

5. The endoscope according to claim 4, wherein the power supply portion comprises:
a switching circuit adapted to generate an ac power by switching a dc power from the battery, and a coil adapted to provide the ac power in non-contact fashion.

6. The endoscope according to claim 4, characterized in that an ac power is supplied in a non-contact fashion to a dc power generation portion provided in the endoscope exterior body through the power supply portion in association with the operation of mounting the housing to the endoscope exterior body.

7. The endoscope according to claim 6, characterized in that charging operation for charging the battery through the charging apparatus starts in association with the operation of mounting the housing to the charging apparatus.

8. The endoscope according to claim 3, characterized in that a dc power generation portion for generating a dc power from an ac power supplied in a non-contact fashion is provided inside the endoscope exterior body in which the housing is mounted.

9. The endoscope according to claim 8, characterized in that the dc power generation portion includes a coil which electro-magnetically couples with an ac power supplied in a non-contact fashion.

10. The endoscope according to claim 1, characterized in that the switching portion is a non-contact switching portion in which switching is performed in a non-contact fashion for an object to be switched.

11. The endoscope according to claim 10, characterized in that the non-contact switching portion is formed of a magneto-sensitive switch which is turned ON/OFF by magnetism.

12. The endoscope according to claim 1, characterized in that the power supplied to the charging apparatus in a non-contact fashion is an ac power, and the charging portion is supplied with the ac power through a non-contact coil.

13. The endoscope according to claim 1, characterized by comprising a remaining amount detection portion for detecting a remaining amount of electric energy of the battery.

14. The endoscope according to claim 1, characterized by comprising means for transmitting the remaining amount of electrical energy of the battery to a display portion.

15. The endoscope according to claim 1, characterized by comprising a connection portion which is provided in the operation portion or in a peripheral portion thereof and to which a tube unit inserted with at least one conduit can be detachably connected.

16. The endoscope according to claim 15, characterized in that a conduit is inserted into the insertion portion, and the conduit is configured such that in the connection portion in the operation portion or the peripheral portion thereof, the tube unit provided with a conduit in communication with the foregoing conduit is detachable.

17. The endoscope according to claim 15, characterized in that there is provided in the peripheral portion including the operation portion a signal transmit portion by wireless communication.

18. The endoscope according to claim 15, characterized by comprising a bending operation apparatus for performing bending operation in the peripheral portion including the operation portion.

19. The endoscope according to claim 1, characterized by comprising a plurality of operation mechanisms of different kinds in the operation portion, and a control processing portion for performing the control processing for the image pickup apparatus, the signal processing portion and the control processing portion for performing control operation for the signal processing portion and the plurality of operation mechanisms inside the operation portion.

* * * * *